(12) United States Patent
Humphrey (10) Patent No.: US 8,968,371 B2
(45) Date of Patent: Mar. 3, 2015

(54) PROXIMAL HUMERUS FRACTURE REPAIR PLATE AND SYSTEM

(71) Applicant: Shoulder Options, Inc., Waxhaw, NC (US)

(72) Inventor: C. Scott Humphrey, Eagle, ID (US)

(73) Assignee: Shoulder Options, Inc., Waxhaw, NC (US)

( * ) Notice: Subject to any disclaimer, the term of this patent is extended or adjusted under 35 U.S.C. 154(b) by 0 days.

(21) Appl. No.: 13/927,581

(22) Filed: Jun. 26, 2013

(65) Prior Publication Data

US 2014/0163623 A1    Jun. 12, 2014

Related U.S. Application Data

(63) Continuation of application No. 13/041,350, filed on Mar. 4, 2011, now abandoned.

(60) Provisional application No. 61/312,201, filed on Mar. 9, 2010.

(51) Int. Cl.
*A61B 17/80* (2006.01)
*A61B 17/17* (2006.01)
*A61B 17/86* (2006.01)

(52) U.S. Cl.
CPC ......... *A61B 17/8057* (2013.01); *A61B 17/1728* (2013.01); *A61B 17/8061* (2013.01); *A61B 17/8004* (2013.01); *A61B 17/864* (2013.01); *A61B 2017/1778* (2013.01)
USPC ............................ 606/289; 606/291; 606/282

(58) Field of Classification Search
CPC ............... A61B 17/80; A61B 17/8052; A61B 17/8057; A61B 17/8004; A61B 17/8009; A61B 17/8014; A61B 17/8061; A61B 2017/1739; A61B 2017/1778
USPC .......... 606/280–282, 286, 289, 291, 96, 902, 606/301, 300, 105, 55, 57–58
See application file for complete search history.

(56) References Cited

U.S. PATENT DOCUMENTS

| | | | | |
|---|---|---|---|---|
| 5,061,181 | A * | 10/1991 | Niznick | 433/174 |
| 6,955,677 | B2 * | 10/2005 | Dahners | 606/287 |
| 2005/0261688 | A1 * | 11/2005 | Grady et al. | 606/69 |
| 2006/0264947 | A1 * | 11/2006 | Orbay et al. | 606/69 |
| 2007/0270853 | A1 * | 11/2007 | Leung | 606/69 |
| 2009/0312760 | A1 * | 12/2009 | Forstein et al. | 606/71 |

OTHER PUBLICATIONS

Zimmer®. "Periarticular Proximal Humeral Locking Plate Surgical Technique.". 2005. <http://depts.washington.edu/shoulder/Surgery/Zimmer_Periarticular_Proximal_Humeral_Locking_Plate_Surgical_Technique_97-2347-041-00_12_2005.pdf> Last Accessed: May 1, 2014.*

* cited by examiner

*Primary Examiner* — Todd Manahan
*Assistant Examiner* — Marcela I Shirsat (57) ABSTRACT

Devices and systems for repairing bone fractures and more specifically a fracture repair plate that provides for fixation of a metaphysis to the diaphysis of a long bone, for instance a fracture between the proximal humerus and the diaphysis of the humerus. The fracture repair system includes an implantable repair fracture repair plate and a bone anchor for fixing the fracture repair plate to a bone. In one embodiment, the fracture repair plate may also be adapted to serve as an anchor for a suture. The fracture repair system may also include a fracture reduction mechanism attachable to the fracture repair plate for imparting a controlled translational movement between two bone segments along a plane that lies substantially parallel to the surface of the bone to which the fracture repair plate is attached and substantially parallel to the longitudinal axis of the bone shaft.

3 Claims, 5 Drawing Sheets

PROXIMAL HUMERUS FRACTURE REPAIR PLATE AND SYSTEM

RELATED APPLICATIONS

This application is a continuation of application Ser. No. 13/041,350 entitled Proximal Humerus Fracture Repair Plate and System. Filed Mar. 4, 2011, which claims the benefit of the filing date of a prior-filed Provisional Application Ser. No. 61/312,201 entitled Long Bone Head Fracture Repair Plate, filed Mar. 9, 2010, each of which is incorporated herein by reference.

FIELD OF THE INVENTION

The present invention relates to a device and system for repairing a fracture of a long bone and more specifically to a fracture repair plate and system that provides for reduction and fixation of a fracture of the humerus bone, for instance a fracture at the surgical neck of the humerus.

BACKGROUND

A fracture repair plate is fastenable to the surface of a bone at the site of a fracture to aid in a repair of the fracture by stabilizing the fracture. Attaching a fracture repair plate for such a purpose with threaded bone screws is well known in the art. As the proximal humerus bone breaks, the fracture lines usually propagate in predictable planes. Based on this, a fracture classification system has been described (the Neer classification system). There are up to 4 large bony fragments that typically result when a proximal humerus bone is fractured. These include: 1) the humeral head, 2) the greater tuberosity, 3) the lesser tuberosity, and 4) the diaphysis or shaft. The rotator cuff tendons attach to the greater and lesser tuberosities. It is usually possible to achieve robust purchase of a screw in the humeral diaphysis and humeral head. However, the greater and lesser tuberosities are often not amenable to screw fixation due to the frailty of these bony fragments. Fortunately, it is still often possible to reduce these fracture fragments to an anatomical position and to achieve acceptable fixation by placing sutures through the rotator cuff tendons at the tendon-bone interface, and then tying those sutures to a plate.

Fractures at the juncture of the metaphysis and diaphysis of a long bone are relatively common, for instance fractures at the surgical neck of the humerus bone. In those instances where such a fracture is complete, it may be beneficial to provide a force substantially along the axis of the diaphysis of the bone to provide a translational force between the bone segments in order to compress or distract the segments in order to reduce the fracture.

A variety of screws and anchoring devices are used in connection with fixing fracture repair plates to bone. Screws employed in conventional means and with known fracture repair devices for the repair of a fracture at the head of a long bone have been seen to back out on occasion. In addition, screws tips may cut through the bone, leading to failure of fracture fixation. Additionally, in the case of comminuted fractures the smaller fragments and their soft tissue connections are not amenable to fixation with screws, but may be more effectively repaired using sutures.

A need exists to provide a fracture repair plate for repairing a fracture of a long bone and more specifically to a fracture repair plate that provides for fixation of a fracture at the surgical neck of the humerus bone. Additionally, a need exists to provide a fracture repair plate that provides for fixation of a proximal humerus to the diaphysis of a long bone. There is also a need for a fracture repair plate for repairing a fracture at the surgical neck of the humerus bone specifically designed to account for the anatomy of the rotator cuff, proximal humeral bony anatomy and contour, and vascular supply of the proximal humerus. Additionally, a need exists for a fracture fixation plate that is optimized to allow the surgeon to use sutures to augment the repair of smaller bony fragments.

Additionally, there is a need for a fracture fixation plate that cooperates with means for providing a translational force between the bone segments in order to compress or distract the segments in order to reduce the fracture. More particularly there is a need for a fracture fixation plate that provides a means for applying a translational force between bone segments capable of imparting a force sufficient to create an impacted interface at the site of the fracture. In addition there is a need to provide means for imparting a translational force between bone segments that capable of being adapted for use with an anatomic right or left fracture repair plate. While the prior art includes translational devices, in each case these devices apply the translational force in a plane defined generally by the upper surface of a fracture repair plate, a plane defined generally by the surface of the diaphysis or in some cases along a plane that lies above both of these.

A need also exists to provide an anchor, and an anchoring system for fixation of fracture repair plates to bone, improving on the devices and systems currently employed for affixing fracture repair plates to the bone. Finally, a need also exists to provide an anchor, and an anchoring system for fixation and anchoring of a proximal humerus to the diaphysis of a long bone, for instance in the case of a fracture at the surgical neck of the humerus bone using a fracture repair plate.

Therefore an object of the present invention is to provide a fracture repair plate for repairing a fracture at the head of a long bone and more specifically to a fracture repair plate that provides for fixation of a proximal end to the diaphysis of a long bone. Another object of the present invention is to provide fracture repair plate for repairing a fracture at the head of a long bone and more specifically to a fracture repair plate that also provides for fixation of a proximal end to the diaphysis of a long bone and for tendon-to-bone repair that may accompany the fracture between the proximal end to the diaphysis of a long bone. Yet another object of the present invention is to provide a fracture repair plate for repairing a fracture at the head of a long bone specifically designed to account for the anatomy of the rotator cuff, proximal humeral bony anatomy and contour, and vascular supply of the proximal humerus. Another object of the present invention is to provide a fracture repair plate that is optimized to facilitate the use of sutures for augmenting the repair of smaller bony fragments and their soft tissue connections. Another object of the present invention is to improve the devices and systems currently employed for affixing fracture repair plates to the bone.

Another object of the present invention is to provide a fracture fixation plate that cooperates with means for providing a translational force between the bone segments in order to compress or distract the segments in aid of reducing the fracture. An additional objective of the present invention is to provide a fracture fixation plate that cooperates with means for providing a translational force between bone segments capable of imparting a force sufficient to create an impacted interface at the site of the fracture. An additional objective of the present invention is to provide means for imparting a translational force between bone segments that capable of being adapted for use with anatomic right and left fracture repair plates. An additional objective of the present invention is to provide means for imparting a translational force between bone segments configured such that the translational force is applied along a plane that intersects the diaphysis and preferably along a plane that lies parallel to and substantially along a longitudinal axis of the diaphysis. An additional objective of the present invention is to provide a device and system for reducing a fracture at the surgical neck of the humerus bone using a fracture repair plate that cooperates with means for providing a translational force between bone segments capable of imparting a force sufficient to create an impacted interface at the site of the fracture. Another object of the present invention is to provide a fracture fixation plate that cooperates with means for providing a translational force between bone segments capable of being adapted for use with an anatomic right or left fracture repair plate.

An additional objective of the invention is to provide an anchor, and an anchoring system for providing fixation of a fracture repair plate to a bone.

SUMMARY OF THE INVENTION

The present invention is directed to devices and systems for repairing a fracture of a long bone. In the preferred embodiment of the invention, the fracture repair plate provides for fixation of a fracture located between a proximal end and the diaphysis of a long bone, for instance the proximal humerus to the diaphysis of the humerus bone. The present invention also includes systems for repairing a fracture of a long bone that include means for imparting a translational force between bone segments to compress or distract the segments in order to reduce the fracture. In a preferred embodiment of the system, the means for imparting a translational force between bone segments is capable of being adapted for use with an anatomic right or left fracture repair plate. In a preferred embodiment of the system, the means for imparting a translational force between bone segments is configured such that the translational force is applied along a plane that lies substantially parallel to and substantially coplanar with a longitudinal axis of the diaphysis.

In a preferred embodiment, the contour of the inner face of the fracture repair plate approximates the contour of a long bone against which the fracture repair plate is intended for use in repairing. In a preferred embodiment, while the contour of the inner face of the fracture repair plate approximates the contour of a long bone against which the fracture repair plate is to be used, the inner face is configured such as to minimize the actual surface area of contact of the inner face of the fracture repair plate and the surface of the bone. For example, a fracture repair plate according to the present invention used in the repair of a fracture involving the proximal humerus would include a shaft attachment segment and a head segment each attached and extending from a transitional neck segment. An inner face contour of the fracture repair plate is configured such that the inner face contour of shaft attachment segment approximates a contour of a proximal lateral surface of the humeral shaft including a part of the crest of the lesser tuberosity, the inner face contour of the transitional neck segment would approximate a contour of a proximal lateral aspect of the surgical neck of the humerus including a lateral portion of the crest of the lesser tuberosity. Similarly, an inner face contour of the head segment would approximate a contour of a proximal lateral aspect of the humerus as defined by the greater tuberosity and the lateral metaphysis.

While the contour of the fracture repair plate approximates the contour of the lateral aspect of the proximal humerus, the fracture repair plate is configured having a bearing surface configured to minimize plate-to-bone contact upon which the fracture repair plate rests against the bone, thereby substantially reducing the surface area of contact of the inner face of the fracture repair plate and the surface of the bone.

It is believed that bone health is improved by avoiding compression of the periosteal tissue by minimizing actual surface area of contact of the inner face of the fracture repair plate and the surface of the bone. This is achieved by purposefully mismatching the radius of curvature of the concave surface of the plate relative to the radius of curvature of the bone.

The generally "D" shaped peripheral configuration of the head segment of the fracture repair plate is designed to follow the contour of the intertubercular groove and the lateral portion of the proximal humerus. More particularly, the generally "D" shaped peripheral configuration of the head segment is configured to accommodate the arcuate artery that branches from the anterior humeral circumflex artery and runs superiorly just lateral to the intertubercular groove. A fracture repair plate according to the present invention for use in the repair of a fracture involving the proximal humerus and diaphysis of the right arm would be the mirror image of a fracture repair plate for use in the repair of a fracture involving the proximal humerus and diaphysis of the left arm.

Apertures formed through the cross-section of the fracture repair plate may include a variety of configurations adapted for a variety or purposes including threaded and un-threaded apertures adapted to accept locking or non-locking screws as well as apertures of various configurations including oblong or slotted aperture adapted to accept non-locking screws.

The present invention is also directed to an anchor and an anchoring system for anchoring a fracture repair plate against a long bone. The preferred anchor includes a shaft portion having a plurality of annular grooves formed about a periphery of the shaft and one or more longitudinal grooves that are formed parallel to a primary axis of the shaft. The anchor also includes a head having an external thread adapted to cooperate with the interior thread formed in an anchor aperture. The anchor is pressed into a hole drilled into the bone such that a "press" or "interference" fit exists between the anchor and the drilled hole. The external thread of the head engages the threads of the anchor aperture and the anchor is tightened and locked to the plate. The annular grooves formed about a periphery of the shaft of the anchor and the longitudinal grooves provide several advantages. First when inserting or withdrawing the anchor from a freshly drilled hole, the longitudinal grooves in particular provide venting for fluid captured in the hole. Additionally as the fracture and the site of insertion of the anchors heal growth of new bone will form in the annular and longitudinal grooves resisting and reducing the possibility of both rotation and pullout of the anchors.

An additional advantage of the anchor of the present invention is found in its blunt tip. It is known that stress risers form in materials including bone at the site of angular transitions and the more acute the transition the greater the propensity for that site being the locus of crack propagation and failure.

In the preferred embodiment, the axis of each screw diverges from a plane perpendicular to an outer face of the fracture repair plate, as well as diverging from the axis of each of the remaining screws. Similarly, the axis of each bone anchor diverges from the axis of each of the remaining bone anchors.

The present invention is also directed to a fracture repair plate that is further configured having a plurality of suture apertures that provide anchoring for sutures that may be employed in a procedure to reduce a fracture of the head of a long bone. An upper peripheral edge of fracture repair plate is configured having an undercut land. One or more suture apertures are formed along an upper peripheral edge of the fracture repair plate through the undercut land. In one embodiment, the suture apertures exhibit an elongated configuration. The undercut peripheral edge of the fracture repair plate contributes to the ease and accommodation of passing a needle and suture through the plate.

DETAILED DESCRIPTION

Figure 1:
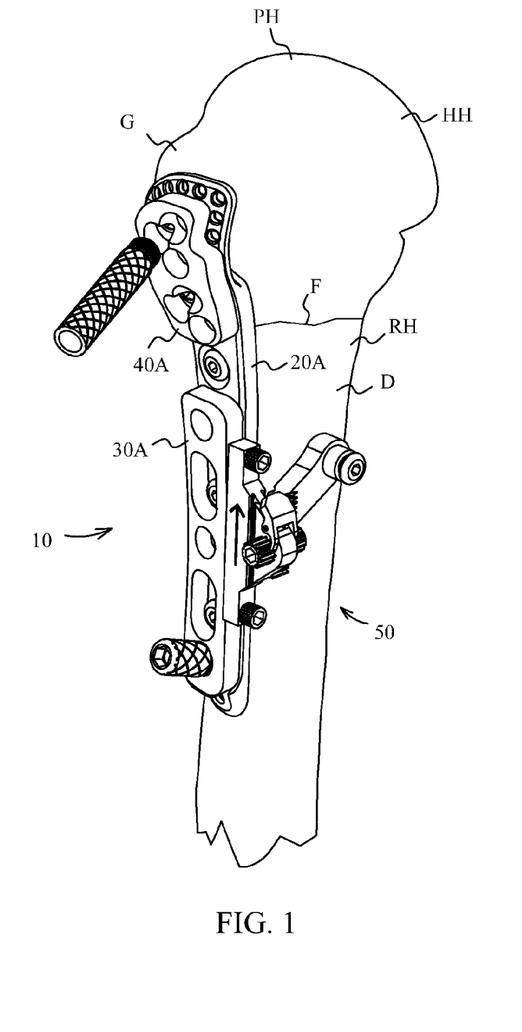
FIG. 1 is a representative perspective view of a proximal humerus fracture repair system including a fracture repair plate according to the present invention.
Figure 2:
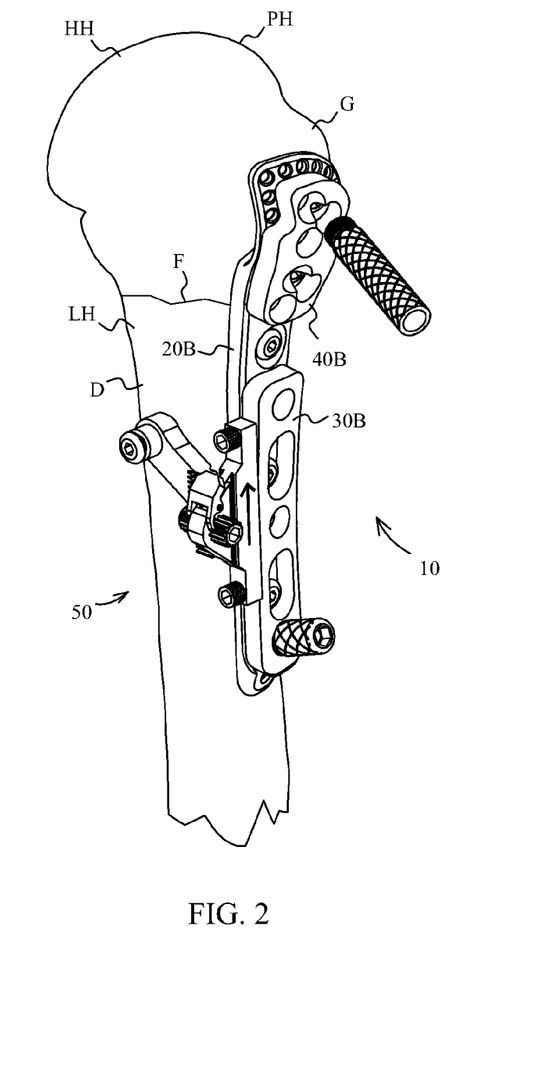
FIG. 2 is a representative perspective view of a proximal humerus fracture repair system including a fracture repair plate according to the present invention.

Referring to FIG. 1, proximal humerus fracture repair system 10 is shown including fracture repair plate 20A attached to a right humerus bone RH including diaphysis D and proximal humerus PH. Proximal humerus PH is shown including humeral head HH and greater turbercle G. Fracture F is a fracture at the surgical neck of the humerus. FIG. 1 shows proximal humerus fracture repair system 10 including first and second right drill guide plates 30A and 40A respectively fixed to outer face 21 of fracture repair plate 20A. Fracture repair plate 20A is specifically adapted for reduction and fixation of a fracture of the right humerus bone RH as seen in FIG. 1. FIG. 2 shows proximal humerus fracture repair system 10 including first and second left drill guide plates 30B and 40B respectively fixed to outer face 21 of fracture repair plate 20B. Reduction mechanism 50 is configured so that it may be adapted for attachment to first right drill guide plate 30A for reduction and fixation of a fracture of the right humerus bone RH as shown in FIG. 1, or in the alternative reduction mechanism 50 may be adapted for attachment to left drill guide plate 30B for reduction and fixation of a fracture of the left humerus bone LH as shown in FIG. 2.

Figure 3:
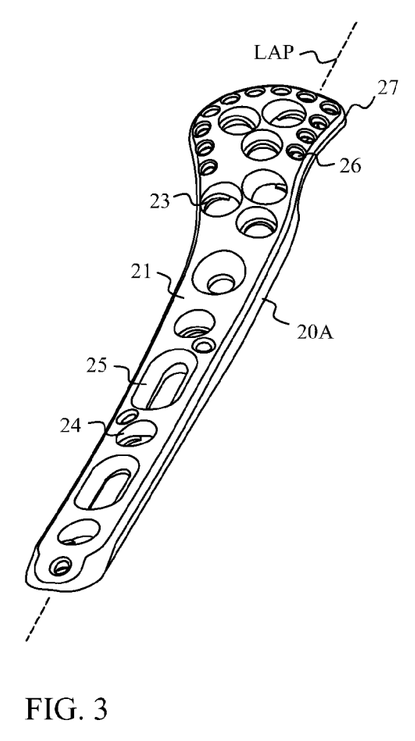
FIG. 3 is a representative perspective view of a fracture repair plate according to the present invention.
Figure 4:
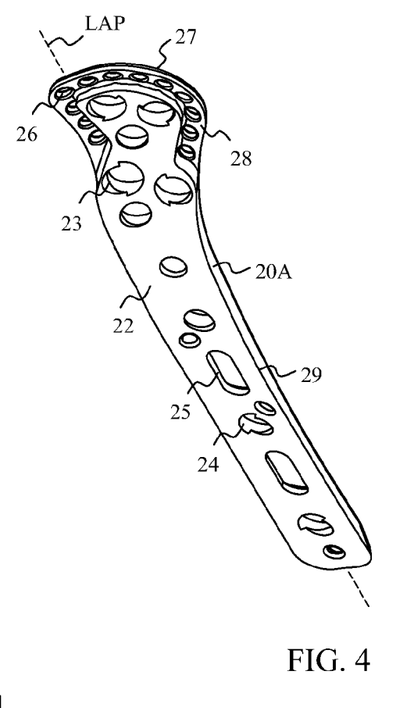
FIG. 4 is a representative perspective view of a fracture repair plate according to the present invention.

Referring to FIGS. 3 and 4 fracture repair plate 20A is shown specifically adapted for reduction and fixation of a fracture of the right humerus bone. Fracture repair plate 20A includes longitudinal axis LAP, outer face 21 as seen in FIG. 3 and a contoured inner face 22 seen in FIG. 4. Preferably, inner face 22 of fracture repair plate 20A is formed having a contour that approximates a contour of the lateral aspect of the proximal humerus to which fracture repair plate 20A is to be attached for a fixation. While the contour of inner face 22 approximates the contour of the lateral aspect of the proximal humerus and diaphysis, fracture repair plate 20A is configured having bearing surface 29 upon which fracture repair plate 20A rests against humerus bone HB. Bearing surface 29 is configured to minimize plate to bone contact substantially reducing the surface area of contact of the inner face of the fracture repair plate and the surface of the bone.

Fracture repair plate 20A is also configured having a plurality of anchor apertures typified by locking bone anchor aperture 23, a plurality of threaded screw apertures typified by locking screw aperture 24 and a pair of slotted screw apertures typified by slotted screw aperture 25. Fracture repair plate 20A also includes a plurality of suture apertures typified by suture aperture 26 formed about upper peripheral edge 27. Referring to FIG. 4 it can be seen that fracture repair plate 20A is formed such that upper peripheral edge 27 includes an undercut land 28 that provides clearance for passage of a suture once fracture repair plate 20A is fastened against the bone.

Figure 5:
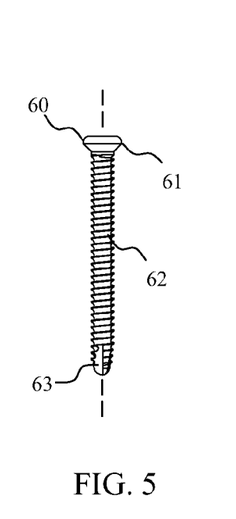
FIG. 5 is a representative front view of a non-locking cortical screw according to the present invention.

A variety of fasteners are use to secure the fracture repair plate of the present invention. FIG. 5 shows non-locking cortical screw 60 including head 61 adapted to accept a polygonal head type driver for instance a hex-headed driver. Non-locking cortical screw 60 also includes threads 62 and self tapping tip 63.

Figure 6:
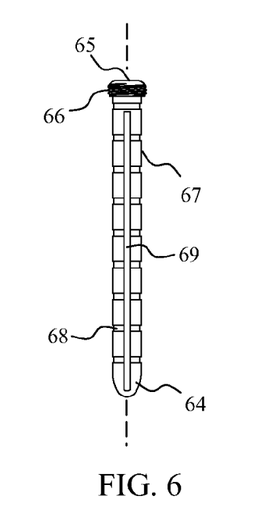
FIG. 6 is a representative front view of a locking bone anchor according to the present invention.

FIG. 6 shows locking bone anchor 65 including head 66 also adapted to accept a polygonal head type driver for instance a hex-headed driver. Locking bone anchor 65 is configured having threaded head 66 adapted to cooperate with a thread formed in each of the anchor apertures typified by locking bone anchor aperture 23, (shown in FIGS. 2 and 3). Locking bone anchor 65 includes shaft 67 having blunt tip 64, a plurality of annular grooves 68 formed about shaft 67 and a plurality of longitudinal grooves 69 formed parallel to a primary axis of shaft 67. Locking bone anchor 65 is pressed into a hole drilled into the bone such that a "press" or "interference" fit exists between shaft 67 and the drilled hole. Threaded head 66 of engages the threads of the threaded anchor aperture and the anchor is tightened and locked. As a fracture and the site of insertion of the locking bone anchors 65 heal, growth of new bone will form in annular grooves 68 and longitudinal grooves 69 resisting and preventing both rotation and pullout of locking bone anchor 65.

Figure 7:
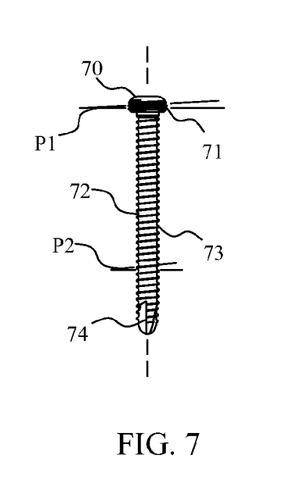
FIG. 7 is a representative front view of a locking cortical screw according to the present invention.

FIG. 7 shows locking diaphyseal screw 70 including threaded head 71 also adapted to accept a polygonal head type driver for instance a hex-headed driver. Locking diaphyseal screw 70 also includes threads 73 formed on shaft 72 and self tapping tip 74. In the preferred embodiment threaded head 71 includes a thread formed at a first thread pitch P1 and threads 73 formed on shaft 72 includes a thread formed at a second thread pitch P2. This feature reduces the tendency of locking diaphyseal screw 70 to back out over time.

Figure 8:
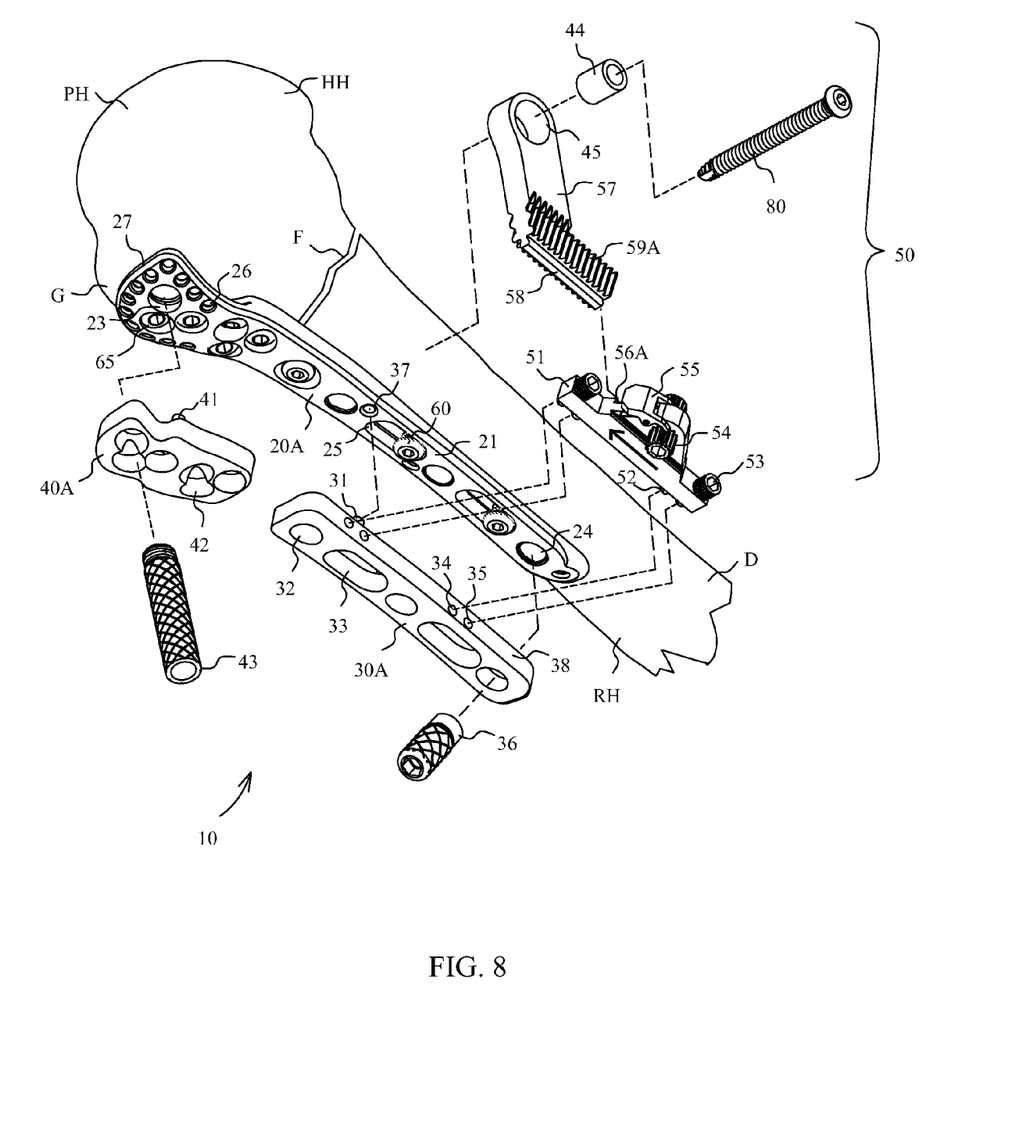
FIG. 8 is a representative perspective exploded view of a proximal humerus fracture repair system including a fracture repair plate according to the present invention.

Referring to FIG. 8, right humerus bone RH is shown including diaphysis D and proximal humerus PH that includes humeral head HH and greater tuberosity G. Fracture F is a commonly seen surgical neck fracture. Right humerus bone RH is shown positioned in a routinely implemented "beach chair position" for reduction and fixation to demonstrate the advantageous positioning of reduction mechanism 50 during a procedure. Proximal humerus fracture repair system 10 is shown with fracture repair plate 20A partially attached to a generally lateral surface of right humerus bone RH with upper peripheral edge 27 fracture repair plate 20A extending over a proximal lateral aspect of the proximal humerus defined in part by the greater tuberosity G. Fracture repair plate 20A includes a plurality of anchor apertures typified by locking bone anchor aperture 23, through which a plurality of locking bone anchors 65 are set. As shown, fracture repair plate 20A includes a pair of slotted screw apertures typified by slotted screw aperture 25. Non-locking cortical screw 60 is shown engaging left humerus LH through slotted screw aperture 25. Fracture repair plate 20A also includes a plurality of threaded screw apertures typified by locking screw aperture 24. A plurality of suture apertures typified by suture aperture 26, are formed through upper peripheral edge 27 of fracture repair plate 20A.

Proximal humerus fracture repair system 10 also includes first right drill guide plate 30A having a plurality of locking screw guide apertures typified by locking screw guide aperture 32 and a plurality of slotted screw guide apertures typified by slotted screw guide aperture 33. As shown first right drill guide plate 30A may be located against outer face 21 of fracture repair plate 20A by inserting a pair of locator pins typified by first drill guide plate locator pin 31 into a pair of corresponding locator pin apertures typified by first drill guide plate locator pin aperture 37. First right drill guide plate 30A may be secured to fracture repair plate 20A by inserting first drill guide 36 through one of several locking screw guide apertures typified by locking screw guide apertures 32 and threadedly engaging the end of first drill guide 36 with one of the plurality of threaded screw apertures typified by locking screw aperture 24.

Proximal humerus fracture repair system 10 also includes second drill guide plate 40A having a plurality of bone anchor apertures typified by bone anchor aperture 42. Second drill guide plate 40A may be located against fracture repair plate 20A by inserting second drill guide plate locator pin 41 into a corresponding suture aperture 26 which serves as a locator pin aperture. Second drill guide plate 40A is secured to fracture repair plate 20A by inserting second drill guide 43 through one of several threaded bone anchor apertures typified by bone anchor aperture 42 and threadedly engaging the end of second drill guide 43 with one of the plurality of locking bone anchor apertures typified by locking bone anchor aperture 23. Both first right drill guide plate 30A and second drill guide plate 40A are adapted to guide a drill at a pre-selected angle.

With continued reference to FIG. 8, proximal humerus fracture repair system 10 also includes reduction mechanism 50. Reduction mechanism 50 includes reduction mechanism body 51 that may be located against upper edge 38 of first right drill guide plate 30A by inserting a pair of reduction mechanism locator pins typified by reduction mechanism locator pin 52 into a corresponding pair of reduction mechanism locator pin apertures typified by reduction mechanism locator pin aperture 34 located on upper edge 38 of first right drill guide plate 30A. Reduction mechanism body 51 is secured against upper side 38 of first right drill guide plate 30A by threadedly engaging a pair of captured screws typified by captured screw 53 with the corresponding threaded aperture located on upper side 38 of first right drill guide plate 30A.

With reduction mechanism body 51 is secured against upper side 38 of first right drill guide plate 30A, dovetail 58 of traction arm 57 is slideably engaged with right dovetail groove 56A of reduction mechanism body 51 with right side rack gear 59A of traction arm 57 engaging right pinion 54A of reduction mechanism body 51. Traction arm 57 is positioned with respect to reduction mechanism body 51 so that as right pinion 54A is rotated against right side rack gear 59A, traction arm 57 moves towards the proximal humerus PH of right humerus RH. Once traction arm 57 is positioned as desired, non-locking screw 80 is inserted through bushing 44 and traction arm aperture 45 and is subsequently driven into diaphysis D of right humerus RH along a traction plane T that lies substantially parallel to surface plane SP said traction plane T passing through a longitudinal axis of diaphysis LAS. Spring biased pawl 55 assures that the position of traction arm 57 may be accurately maintained with respect to reduction mechanism body 51 throughout a procedure.

Figure 9:
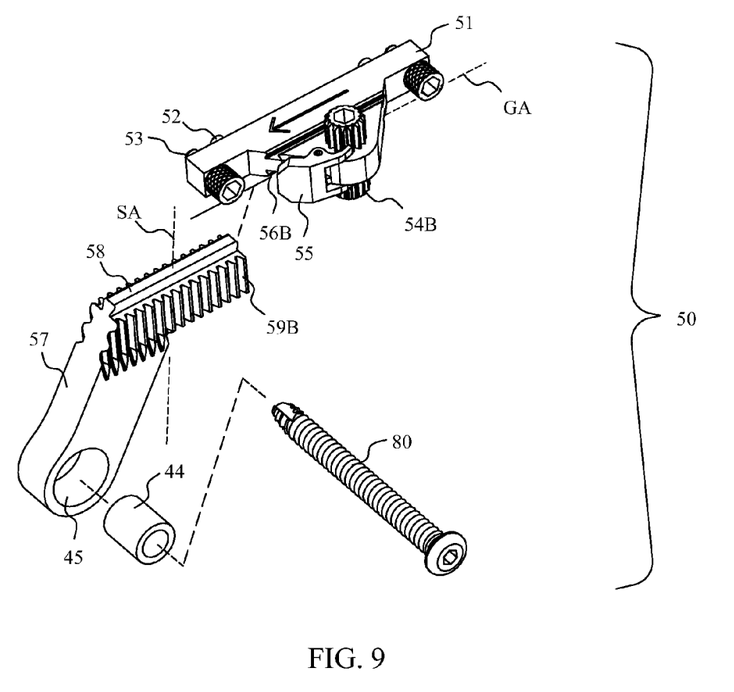
FIG. 9 is a representative perspective exploded view of a reduction mechanism according to the present invention.

FIG. 9 shows reduction mechanism 50 adapted for attachment to first left drill guide plate 30B, (as shown in FIG. 2), for reduction and fixation of a fracture of the left humerus bone LH, (as shown in FIG. 2). For use in the reduction and fixation of a fracture of the left humerus bone, reduction mechanism body 51 is rotated one-hundred and eighty degrees about dovetail groove axis GA and traction arm 57 is rotated one-hundred and eighty degrees about traction arm axis TA that is perpendicular to dovetail 58 of traction arm 57. Dovetail 58 of traction arm 57 then slideably engages with left dovetail groove 56B with left side rack gear 59B of traction arm 57 engaging left side pinion 54B of reduction mechanism body 51. Once traction arm 57 is positioned as desired, non-locking screw 80 may be inserted through bushing 44 and traction arm aperture 45 in preparation to driving into diaphysis D of left humerus LH, (as shown in FIG. 2). Spring biased pawl 55 assures that the position of traction arm 57 may be accurately maintained with respect to reduction mechanism body 51 throughout a procedure.

Figure 10:
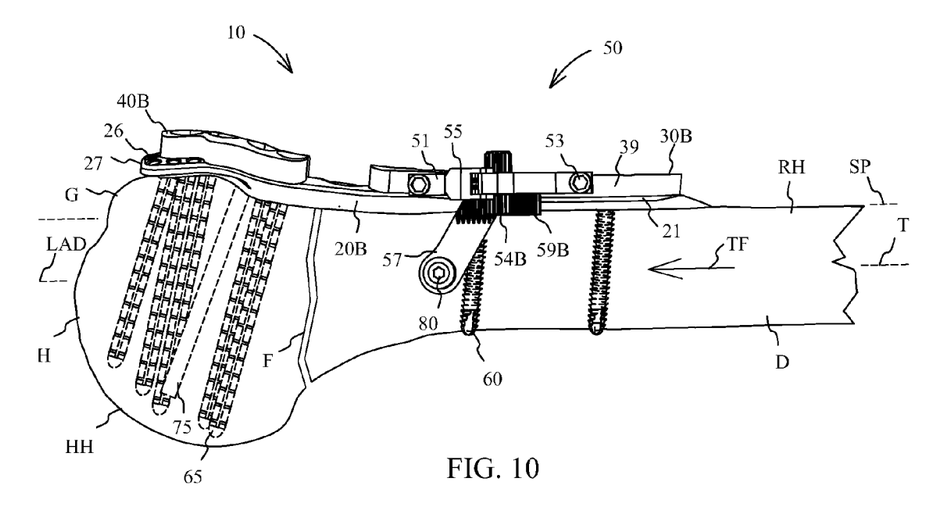
FIG. 10 is a representative medial side view of a proximal humerus head fracture repair system including a fracture repair plate according to the present invention.

FIG. 10 shows left humerus bone LH having fracture F located between diaphysis D and proximal humerus PH. Proximal humerus fracture repair system 10 is shown with fracture repair plate 20B partially attached to a generally lateral surface of left humerus bone LH. In use, once secondary or tertiary fractures if any of proximal humerus PH have been stabilized, fracture repair plate 20B is positioned against diaphysis D of left humerus bone LH with upper peripheral edge 27 fracture repair plate 20B extending over a proximal lateral aspect of proximal humerus PH defined in part by the greater tuberosity G. A pair of pilot holes are drilled into diaphysis D, one each at location corresponding to the pair of slotted apertures typified by slotted aperture 25, (shown in FIG. 8). A pair of non-locking cortical screws 60 are set into each of the pair of drilled pilot holes and fracture repair plate 20B is adjusted lengthwise on diaphysis D along an axis of the slotted apertures to a desired position relative to the bone and non-locking cortical screws 60 are tightened.

Next, first left drill guide plate 30B and second left drill guide plate 40B are attached to outer face 21 of fracture repair plate 20B and a plurality of bone anchor holes typified by bone anchor hole 75 are drilled employing second left drill guide plate 40B. A pattern of bone anchor holes are drilled into proximal humerus PH or bone fragments thereof. According to the preferred embodiment of the invention each bone anchor hole drilled for one of the plurality of bone anchors is drilled at a specified angle so that an axis of each hole differs and diverges from the angle of the axes of each of the remaining holes. As the bone anchor holes 75 are drilled bone anchors 65 are set. Preferably a fit between each locking bone anchor 65 and its respective bone anchor hole 75 is characterized as a "press" or "interference" fit.

Once proximal humerus PH is anchored against fracture repair plate 20B, reduction mechanism body 51 of reduction mechanism 50 is secured against upper side 39 of first left drill guide plate 30B by a pair of captured screws typified by captured screw 53. Traction arm 57 slideably engages reduction mechanism body 51 and traction arm 57 is positioned so that adequate forward travel of traction arm 57 may be achieved. Once so positioned, traction are 57 is secured to diaphysis D of left humerus bone LH by non-locking screw 60. As seen in FIG. 10 another unique aspect of the present invention lies in the fact that diaphysis D and proximal humerus PH of left humerus bone LH are each capable only of a single degree of movement with respect to one another, that being movement along a line defined by longitudinal axis of the diaphysis LAD, while secured by the placement of locking bone anchors 65, the two non-locking cortical screws 60 placed through fracture repair plate 20B and non-locking cortical screw 80 set through traction arm 57 of reduction mechanism 50.

Once reduction mechanism 50 is secured against first left drill guide plate 30B, non-locking screws 60 are loosened so that diaphysis D of left humerus bone LH is free to move with the advance of traction arm 57. Left pinion 54B is rotated against left side rack gear 59B such that controlled movement of traction arm 57 and therefore the attached diaphysis D towards proximal humerus PH is achieved. Spring biased pawl 55 assures that the position of traction arm 57 is accurately maintained as a translational force TF is applied substantially along a longitudinal axis of the diaphysis LAD of left humerus bone LH. Translational force TF between diaphysis D and proximal humerus PH is sufficient to create an impacted interface or impacted zone at the site of the fracture. Once diaphysis D is positioned as desired with respect to proximal humerus PH, non-locking screws 60 are once again tightened so that diaphysis D will maintain the desired position with respect to proximal humerus PH.

Figure 11:
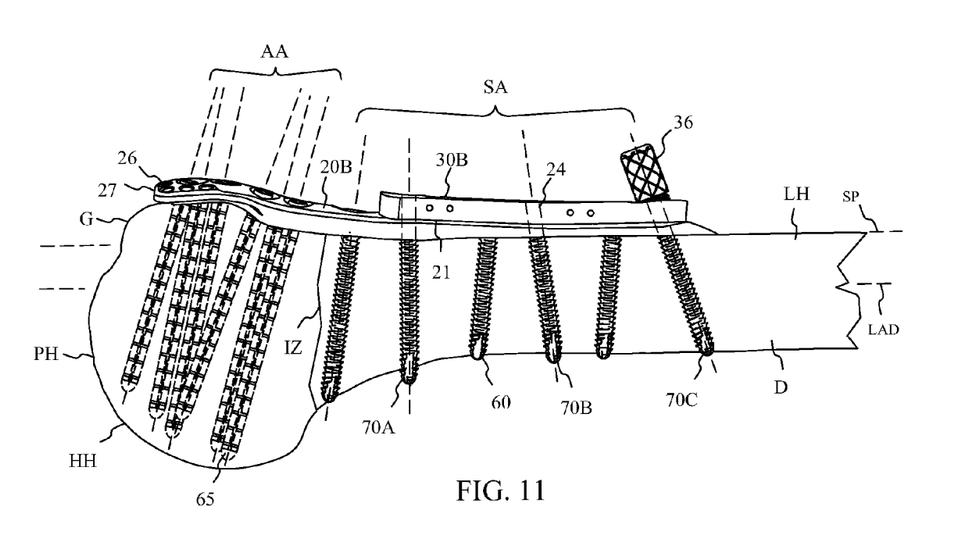
FIG. 11 is a representative medial side view of a proximal humerus fracture repair system including a fracture repair plate according to the present invention.
Figure 12:
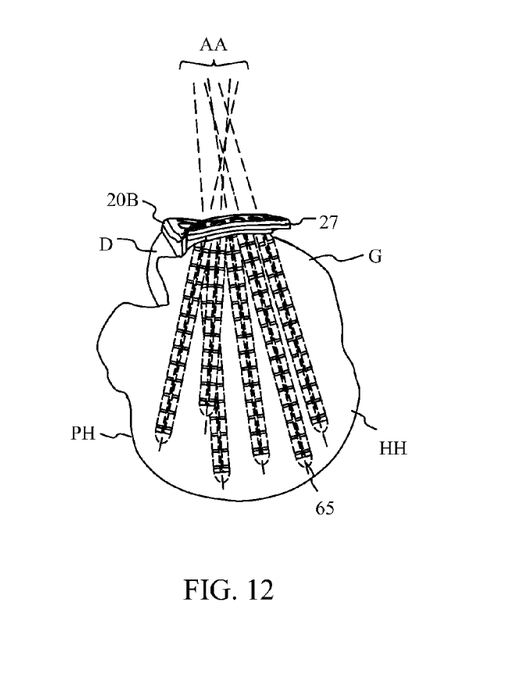
FIG. 12 is a representative proximal view of a proximal humerus fracture repair system including a fracture repair plate according to the present invention.

Referring to FIGS. 11 and 12, show fracture repair plate 20B attached to a generally lateral surface of left humerus bone LH against diaphysis D with upper peripheral edge 27 fracture repair plate 20B extending over a proximal lateral aspect of proximal humerus PH defined in part by the greater tuberosity G. Referring to FIG. 11, once an impacted zone IZ has been established as described above, locking diaphyseal screws 70A-70C may be set. Pilot holes are drilled for locking diaphyseal screws 70A-70C using drill guide 36 to assure that the screw are set at the determined angles. Each pilot hole for locking diaphyseal screws 70A-70C is drilled on a screw axis SA that is divergent from the longitudinal axis of the diaphysis LAD, that angle also being divergent from a screw axis SA of each of the remaining locking diaphyseal screws 70A-70C. As shown in FIG. 11, an angle of screw axis SA for each locking diaphyseal screw 70A-70C and correspondingly an angle of an axis at which each of the locking screw apertures 24 are formed relative to outer face 21 and surface plane SP, defined generally as the surface of the lateral aspect of left humerus bone LH increases progressively as the location of the diaphyseal screws 70A-70C move further distally down diaphysis D and fracture repair plate 20B. More particularly, in the preferred embodiment, screw axis SA for first diaphyseal screw 70A measures ninety degrees, the screw axis SA for second diaphyseal screw 70B measures one-hundred, and the screw axis SA for third diaphyseal screw 70B measures one-hundred and ten degrees. This configuration provides an increased resistance to pullout of the screws which in turn would lead to a failure of the repair.

FIGS. 11 and 12 also show the divergence of anchor axes A of locking bone anchors 65. As seen in the referenced figures, each of the plurality of locking bone anchors 65 is pressed into a hole drilled on anchor axis AA that is divergent from the longitudinal axis of the diaphysis LAD and surface plane SP, (Shown in FIG. 11), that angle also being divergent from an anchor axis AA of each of the remaining locking bone anchors 65. Correspondingly each of the bone anchor apertures 23, shown in FIG. 8, diverge from an anchor axis AA of each of the remaining bone anchor apertures 23.

While this invention has been described with reference to the described embodiments, this is not meant to be construed in a limiting sense. Various modifications to the described embodiments, as well as additional embodiments of the invention, will be apparent to persons skilled in the art upon reference to this description. It is therefore contemplated that the appended claims will cover any such modifications or embodiments as fall within the true scope of the invention.

I claim:

1. A fracture repair system (10) comprising a fracture repair late (20A, 20B) for repairing a fracture at the head of a long bone, the long bone defined in part by a proximal head (PH), a diaphysis (D) including a longitudinal axis (LAD) and a lateral aspect defining in part a surface plane of the diaphysis (SP), the fracture repair plate comprising:
 a longitudinal axis (LAP) that is configured to be parallel to the diaphysis longitudinal axis (LAD), an outer face (21), and a contoured inner face (22), the contoured inner face (22) including a bearing surface (29) configured to contact at least a portion of the lateral aspect of the long bone;
 a head segment at the proximal end of the fracture repair plate, wherein the contoured inner face (22) approximates a contour of the lateral aspect of the proximal head of the long bone;
 a transition neck segment wherein the contoured inner face (22) approximates a contour of the lateral aspect of the long bone between the head and the diaphysis; and
 a shaft attachment segment at the distal end of the fracture repair plate, wherein the contoured inner face (22) approximates a contour of the lateral aspect of the of the diaphysis;
 two or more threaded locking anchor apertures (23) formed through the head segment of the fracture repair plate, each of the two or more threaded locking anchor apertures having an axis that is divergent from the axis of each remaining two or more locking anchor apertures;
 two or more threaded locking screw as apertures (24), formed through the shaft attachment segment of the fracture repair plate, each of the threaded locking screw apertures having a screw axis (SA), characterised in that an angle of the screw axis (SA) of each of the threaded locking screw apertures relative to the outer face (21) of the fracture repair plate (20A, 20B) increases progressively from the proximal to the distal portion of the shaft attachment segment of the fracture repair plate along a line that is configured to be parallel to the diaphysis longitudinal axis (LAD);
 a reduction mechanism (50) including a body (51) adapted for attachment to the drill guide plate (30A, 30B) and a traction arm (57) adapted to engage the body, the traction arm adapted for controlled translational movement relative to the body, the traction arm further adapted for attachment to the bone, such that as a translational force is applied to the traction arm, the translational force is applied to the bone along a plane that lies substantially parallel to the surface plane and substantially parallel to the longitudinal axis of the diaphysis, wherein the reduction mechanism (50) further comprises:
 the body (51) including a right dovetail groove (56A) and a left dovetail groove (56B);

the traction arm (57) including a dovetail (58) slideably engageable with the right dovetail groove adapted to apply the translational force between two bone segments of a long bone;

a pinion gear (54) connected to the body, the pinion gear rotatable relative to the body (51);

the traction arm (57) including a rack gear (59) engageable with the pinion gear such a rotational force applied to the pinion gear provides a translational movement of the traction arm; and a spring biased pawl (55) attached to the body and engageable with the pinion to eliminate counter-rotation of the pinion.

2. A fracture repair system (10) comprising a fracture repair plate (20A, 20B) for repairing a fracture at the head of a long bone, the long bone defined in part by a proximal head (PH), a diaphysis (D) including a longitudinal axis (LAD) and a lateral aspect defining in part a surface plane of the diaphysis (SP), the fracture repair comprising:

a longitudinal axis (LAP) that is configured to be parallel to the diaphysis longitudinal axis (LAD), an outer face (21), and a contoured inner face (22), the contoured inner face (22) including a bearing surface (29) configured to contact at least a portion of the lateral aspect of the long bone;

a head segment at the proximal end of the fracture repair plate, wherein the contoured inner face (22) approximates a contour of the lateral aspect of the proximal head of the long bone, the head segment comprising an undercut land (28) along an upper peripheral edge (27) of the head segment, wherein the undercut land (28) extends beyond the bearing surface (29) and does not contact the long bone;

a transition neck segment wherein the contoured inner face (22) approximates a contour of the lateral aspect of the long bone between the head and the diaphysis; and a shaft attachment segment at the distal end of the fracture repair plate, wherein the contoured inner face (22) approximates a contour of the lateral aspect of the of the diaphysis;

wherein the contoured inner face (22) of any one or more of the head segment, the transition neck segment and the shaft attachment segment has a concave radius of curvature that does not match a radius of curvature of the long bone, thereby effectively reducing the area of the bearing surface (29) that contacts the long bone;

two or more threaded locking anchor apertures (23) formed through the head segment of the fracture repair plate, each of the two or more threaded locking anchor apertures having an axis that is divergent from the axis of each remaining two or more locking anchor apertures;

two or more threaded locking screw as apertures (24), formed through the shaft attachment segment of the fracture repair plate, each of the threaded locking screw apertures having a screw axis (SA), characterised in that an angle of the screw axis (SA) of each of the threaded locking screw apertures relative to the outer face (21) of the fracture repair plate (20A, 20B) increases progressively from the proximal to the distal portion of the shaft attachment segment of the fracture repair plate along a line that is configured to be parallel to the diaphysis longitudinal axis (LAD), wherein the progressive increase in the angle of the screw axis (SA) between each of the two or more threaded locking screw apertures (24) is ten degrees;

a drill guide plate (30A, 30B) attachable to at least a portion of the outer face of the fracture repair plate (20A, 20B), the drill guide plate including a plurality of guide apertures (32, 33) adapted to guide a drill at a pre-selected angle; and a reduction mechanism (50) including a body (51) adapted for attachment to the drill guide plate (30A, 30B) and a traction arm (57) adapted to engage the body, the traction arm adapted for controlled translational movement relative to the body, the traction arm further adapted for attachment to the bone, such that as a translational force is applied to the traction arm, the translational force is applied to the bone along a plane that lies substantially parallel to the surface plane and substantially parallel to the longitudinal axis of the diaphysis, wherein the reduction mechanism (50) further comprises:

the body (51) including a right dovetail groove (56A) and a left dovetail groove (56B);

the traction arm (57) including a dovetail (58) slideably engageable with the right dovetail groove adapted to apply the translational force between two bone segments of a long bone;

a pinion gear (54) connected to the body, the pinion gear rotatable relative to the body (51);

the traction arm (57) including a rack gear (59) engageable with the pinion gear such a rotational force applied to the pinion gear provides a translational movement of the traction arm; and a spring biased pawl (55) attached to the body and engageable with the pinion to eliminate counter-rotation of the pinion.

3. The fracture repair system (10) of claim 2 further comprising:

two or more locking cortical screws (70) adapted for placement through one of the one or more locking screw apertures (24), each of the two or more threaded locking cortical screws including a head (71) attached to a threaded shaft (72), the head of each of the two or more threaded locking cortical screws including a thread (73), each of the one or more locking cortical screws adapted for threaded engagement with the bone, the thread of the head each of the two or more threaded locking cortical screws adapted to engage one of the two or more threaded locking screw apertures; and two or more locking bone anchors (65) adapted for placement through one of the two or more threaded locking anchor apertures (23), each of the two or more locking bone anchors including a plurality of annular grooves (68) formed about a shaft (67) of the locking bone anchor and a plurality of longitudinal grooves (69) formed parallel to a primary axis of the shaft, each of the two or more locking bone anchors including a head (66) attached to the shaft, the head having an external thread adapted to cooperate with the thread formed in one of the two or more threaded locking anchor apertures.

one or more slotted apertures formed through the fracture repair plate;

one or more screws adapted for placement through each of the one or more slotted apertures, the one or more screws adapted for engagement with the long bone; and one or more suture apertures formed along the upper peripheral edge (27) of the plate through the undercut land (28);

wherein the long bone is a humerus and wherein the fracture repair plate is adapted for attachment to an anatomic right humerus or an anatomic left humerus; and wherein the head segment of the fracture repair plate has a generally D shaped peripheral configuration designed to follow a contour of an intertubercular groove of the proximal humerus.

* * * * *